United States Patent [19]

Maggioni et al.

[11] Patent Number: 4,542,229
[45] Date of Patent: Sep. 17, 1985

[54] PROCESS FOR PREPARING 2,3-DIHYDRO-2,2-DIMETHYLBENZOFURAN-7-OL

[75] Inventors: Paolo Maggioni, Montevecchia; Francesco Minisci, Milan; Mariano Correale, Bonate Sotto, all of Italy

[73] Assignee: Brichima S.p.A., Milan, Italy

[21] Appl. No.: 483,612

[22] Filed: Apr. 11, 1983

[30] Foreign Application Priority Data

Apr. 19, 1982 [IT] Italy ................ 20803 A/82

[51] Int. Cl.$^4$ ............................................ C07D 307/86
[52] U.S. Cl. ..................................... 549/462; 568/652
[58] Field of Search ........................ 549/462; 568/652

[56] References Cited

U.S. PATENT DOCUMENTS

| | | | |
|---|---|---|---|
| 4,250,333 | 2/1981 | Rakoutz | 568/652 |
| 4,252,985 | 2/1981 | Rakoutz | 568/652 |
| 4,263,462 | 4/1981 | Michelet et al. | 568/652 |
| 4,321,204 | 3/1982 | Büttner et al. | 549/462 |
| 4,390,733 | 6/1983 | Campolmi et al. | 568/652 |

OTHER PUBLICATIONS

Dehmlow et al., Phase Transfer Catalysis-Verlag Chemie, (1980) pp. 1–11.
Synthesis, No. 4, Apr. 1973, p. 209 "2,5-Dimethylfuran, An Application of Ion Exchange-Resin Catalysis in Organic Synthesis", Scott et al.

*Primary Examiner*—Henry R. Jiles
*Assistant Examiner*—Bernard I. Dentz
*Attorney, Agent, or Firm*—Stevens, Davis, Miller & Mosher

[57] ABSTRACT

A process is described for preparing 2,3-dihydro-2,2-dimethylbenzofuran-7-ol (I), which is a useful intermediary in the preparation of Carbofuran, a known multifunctional insecticide.

The process consists essentially of reacting the pyrocatechol and a methallylhalide in an inert organic solvent in the presence of a solid inorganic base and a suitable catalyst, to obtain o.methallyloxyphenol with high conversion and high selectivity; this product is thermally transposed to o.methallylpyrocatechol, which is finally cyclized to the product (I) by heterogeneous catalysis in the presence of solid acid catalysts.

All stages of the process can be carried out in a single reaction medium, without separating intermediate products.

14 Claims, No Drawings

PROCESS FOR PREPARING 2,3-DIHYDRO-2,2-DIMETHYLBENZOFURAN-7-OL

This invention relates to a new industrial process for preparing 2,3-dihydro-2,2-dimethylbenzofuran-7-ol of formula:

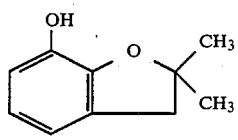  (I)

which is a product useful as an intermediate in the synthesis of 2,3-dihydro-2,2-dimethylbenzofuran-7-ol methylcarbamate of formula:

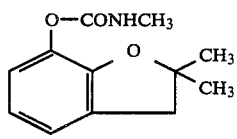

a widely used multi-functional insecticide known commercially by the common name of Carbofuran.

The process according to the invention uses pyrocatechol and a methallyl halide as its starting substances, these being reacted in accordance with the following reaction sequence, preferably but not necessarily in a single reaction medium without separating intermediate products:

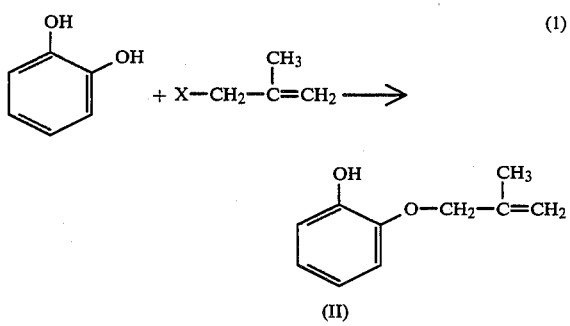

where X is Cl, Br or I

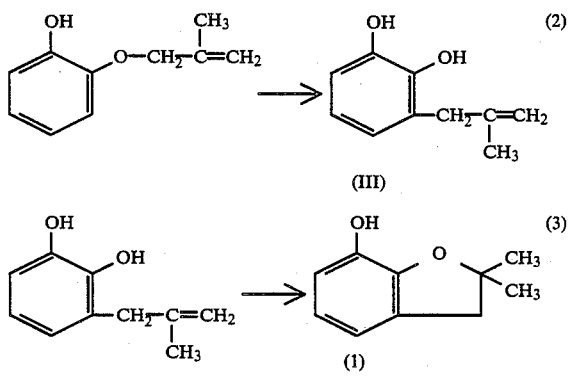

Stage (1), in which the pyrocatechol mono-methallylether (2) is prepared, is carried out in an inert organic solvent, in the presence of an alkaline base in the solid state and catalytic quantities of a quaternary ammonium or phosphonium salt or a crown ether.

The pyrocatechol and methallyl halide are reacted in a molar ratio of between 0.5 and 1.5.

The molar ratio of the pyrocatechol to the alkaline base is between 2 and 0.4. The ammonium, phosphonium or crown ether catalyst is used in a quantity of between 0.01 and 0.8 moles per base equivalent. All the aforesaid ratios are preferred, but are not critical.

The reaction is carried out in an inert gas atmosphere at a temperature of between 40° and 120° C.

The inert organic solvent can be chosen from large classes of compounds such as hydrocarbons (for example n-heptane, cyclohexane, decalin, toluene, xylenes), halogenated hydrocarbons (for example chlorobenzene, dichlorobenzene, 1,2-dichloroethane), alcohols (for example amyl alcohols, hexyl alcohols, heptyl alcohols), ethers (for example $C_6$-$C_{12}$ aliphatic ethers, arylalkyl ethers, cyclic ethers), ketones (for example $C_6$-$C_{12}$ aliphatic ketones, aryl ketones, cyclic ketones), or aliphatic or aromatic nitriles. The essential condition which must be satisified by the solvent is that it must be able to dissolve the pyrocatechol, the methallyl halide and the catalyst, whereas the base must remain present as an undissolved solid phase. It is preferable to operate with a solvent immiscible with water when the entire cycle is carried out in a single solvent, because in this manner the catalyst can be recovered from the solution by simply washing with water, and then recycled.

Because of the large range of solvents which can be used for carrying out the selective mono-etherification of pyrocatechol according to this new process, it is possible to choose a solvent which is also suitable for carrying out the subsequent stages (2) and (3), so that the entire operational cycle proceeds in a single reaction medium, as mentioned above. In particular, because a temperature exceeding 130° C. is required in stage (2), it is preferable to choose a solvent having a boiling point exceeding 130° C. for the first stage, so that it does not become necessary to carry out the transposition of stage (2) under pressure.

It is also possible to advantageously use mixtures of solvents, including those with very different polarities.

The use of solvent mixtures can be useful for example in facilitating catalyst recovery. In this respect, if a high boiling solvent in which the catalyst is poorly soluble (for example a hydrocarbon) is used in mixture with a low boiling polar solvent (for example an alcohol) which dissolves the catalyst, the low boiling solvent can then be removed when the reaction of stage (1) is terminated, so that the catalyst separates and can thus be recovered and recycled with ease.

The preferred methallyl halide for the reaction is the chloride.

The alkaline base used is preferably Na carbonate or hydroxide.

The quaternary ammonium salt used as catalyst is preferably chosen from the group comprising compounds of formula:

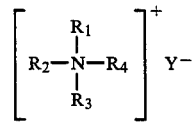

in which $R_1$, $R_2$, $R_3$, $R_4$ are equal or different $C_1$–$C_{18}$ hydrocarbon radicals, possibly substituted, and Y is a halide, sulphuric or sulphonic ion.

The phosphonium salt used as catalyst is chosen from the group of compounds of general formula:

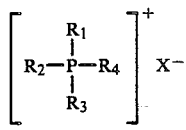

in which $R_1$, $R_2$, $R_3$, $R_4$ are $C_2$–$C_{10}$ hydrocarbon radicals, and X is a halide ion, preferably Cl or Br.

The presence of a catalyst chosen from the aforesaid classes is absolutely necessary for the described process to be applied in an industrial setting.

The reason for this is that if the catalyst is absent, the reaction does not proceed at all if certain solvents are used, wheres with other solvents it proceeds so slowly and in such a poorly selective manner as to be practically unusable.

The mono-etherification of pyrocatechol with alkyl halides, and in particular with methallyl chloride in accordance with equation (1) has already been described. The numerous bibliographical sources on the subject all indicate the difficulty of this reaction, or more precisely the difficulty of carrying out the reaction industrially because of the low pyrocatechol conversion and the poor selectivity leading to the formation of large percentages of by-products. The main by-products which form are the diether, o.methallylpyrocatechol. o.isobutenylpyrocatechol, and p.methallylpyrocatechol. Of these by-products the o.methallylpyrocatechol and o.isobutenylpyrocatechol react in the subsequent stages in the same manner as the main product and are therefore useful products, whereas the diether and the p.methallylpyrocatechol are not only unusable products, but are difficult to separate from the monoether (II), and thus make purification of this latter compound complicated and difficult.

With regard to pyrocatechol conversion, it is known that the formation of by-products is limited at low conversion levels, but the recovery and recycling of the unreacted pyrocatechol considerably affects the economy of the process. At higher conversion levels, the formation of by-products increases strongly.

The most recent and most improved known processes for carrying out reaction (1) are those described in Belgian patent 877,243—Philagro, and in DOS 2932458—Bayer AG.

The Philagro patent is characterised by carrying out the reaction in a double aqueous-organic phase in the presence of a phase transfer catalyst. Compared with this process, new process (1) described above has the advantage of being carried out in a single phase and therefore of not requiring any separation of the two phases before passing to the transposition reaction, thus considerably simplifying the process at the industrial level.

In addition, the new process is much more selective in total useful products, because the catalyst and pyrocatechol are completely in solution in the required proportions, whereas when a double aqueous-organic phase system is used, the pyrocatechol and catalyst are divided between the two phases, where they are present in different proportions depending upon the strength of the solvent and the pH of the medium.

The Bayer patent is characterised by carrying out the etherification reaction in a quite specific and critical organic solvent, namely a polyhydroxyalkylether, containing at least one free hydroxyl. Compared with this process, the new process described above has significant advantages, of which the essential ones are that it can use more industrially acceptable and less costly solvents, in particular solvents which do not require the use of pressure in the subsequent transposition stage and which are much easier to recover, it enables considerably higher reaction rates to be obtained, and is more selective at higher conversion levels.

The second stage of the process according to the present invention is that in which the pyrocatechol mono-methallyl ether (II) is transposed thermally into o.methallylpyrocatechol (III) in accordance with equation (2), by heating the solution originating from stage (1) at a temperature of between 130° and 200° C. in an inert gas atmosphere, after separating the catalyst by simply washing with water or with aqueous acid solutions or by making it insoluble, the catalyst is recovered and recycled.

This stage is carried out in a conventional manner. As already stated, if the solvent or solvent mixture used in stage (1) is suitably chosen, stage (2) can be carried out at ordinary pressure.

Stage (3), in which the o.methallylpyrocatechol and possibly the o.isobutenylpyrocatechol formed as a by-product are cyclised to 2,3-dihydro-2,2-dimethylbenzofuran-7-ol, is carried out by adding a heterogenous acid catalyst to the solution, which is kept under stirring for some hours at 10°–150° C.

Sulphonic acid resins such as Amberlist and Nafion have been found to be particularly effective and industrially interesting catalysts, and are used in quantities of between 1 and 50% by weight of the product to be cyclised.

The cyclisation represented by equation (3) has already been described in the literature (DOS 2932458-Bayer Ag). However, up to the present time this reaction has always been carried out with soluble catalysts in the homogeneous phase.

The fact that the reaction can now be carried out using heterogeneous catalysts is highly advantageous, in that it enables the catalyst used to be practically separated and recovered without loss of catalytic activity, by simple filtration or decantation.

A soluble catalyst, whether recovered or not, must in all cases be separated from the reaction products, and thus in any case complicates the production cycle.

Some practical embodiments are given hereinafter in order to better illustrate the new process according to the present invention, but without in any way limiting it. Examples 1–8 and 10 specifically illustrate stage (1) of the new process in a certain number of possible variations, and the results are compared with the most significant of the known art, whereas examples 9 and 11 illustrate the process in all three stages up to the preparation of the final product (I).

EXAMPLE 1

121 g (1.1 moles) of pyrocatechol, 880 ml of decalin, 51.6 g (0.16 moles) of tetrabutylammonium bromide (TBDB), 135.8 g (1.5 moles) of methallyl chloride, 116.6 g of sodium carbonate (1.1 moles) and 1.8 g of sodium hydrosulphite are fed into a two liter four-neck flask fitted with a condenser, stirrer, thermometer and nitrogen inlet.

The mixture is heated to 80° under stirring in a nitrogen atmosphere. After 6 hours, gas chromatography analysis shows the following product composition in solution: o.methallyloxyphenol 31%, o.dimethallyloxybenzene 1%, pyrocatechol 58.7%, o.methallylprotcatechol 2.7%, p.methallylpyrocatechol 3.3%, o.isobutenylpyrocatechol 1.6%, various impurities 1.7%.

The conversion is 41.3%, the yield of o.methallyloxyphenol is 75% with respect to the converted pyrocatechol, the yield of useful products (o.methallyloxyphenol, o.methallylpyrocatechol, o.isobutenylpyrocatechol) is 85.5% with respect to the converted pyrocatechol.

Only traces of o.methallyloxyphenol are obtained under the same conditions if TBAB is absent.

EXAMPLE 2

The procedure of Example 1 is followed, but using n-heptane as solvent instead of the decalin. Gas chromatography analysis shows the following product composition in solution at the end of the reaction: o.methallyloxyphenol 37.1%, o.dimethallyloxybenzene 0.5%, pyrocatechol 40.4%, o.methallylpyrocatechol 8.4%, p.methallylpyrocatechol 9%, o.isobutenylpyrocatechol 3.8%, various impurities 0.6%.

The conversion 59.6%, the yield of o.methallyloxyphenol is 67.8% with respect to the converted pyrocatechol, and the yield of useful products (o.methallyloxyphenol, o.methallylpyrocatechol, o.isobutenylpyrocatechol) is 82.7% with respect to the converted pyrocatechol.

Only traces of o.methallyloxyphenol are obtained under the same conditions if TBAB is absent.

EXAMPLE 3

The procedure of Example 1 is followed, using p.xylene as solvent instead of the decalin. Gas chromatography analysis shows the following composition of the reaction mixture: o.methallyloxyphenol 23.5%, o.dimethallyloxybenzene 0.2%, pyrocatechol 66%, o.methallylpyrocatechol 1.7%, p.methallylpyrocatechol 7.7%, various impurities 0.9%.

The conversion is 34%, the yield of o.methallyloxyphenol is 69% with respect to the converted pyrocatechol, and the yield of useful products (o.methallyloxyphenol, o.methallylpyrocatechol) is 74% with respect to the converted pyrocatechol.

Only traces of o.methallyloxyphenol are obtained under the same conditions if TBAB is absent.

EXAMPLE 4

The procedure of Example 3 is followed, using an equivalent quantity of Arquad DMMGB (dimethyllaurylbenzyl ammonium chloride) as catalyst instead of the TBAB.

The conversion is 46%, whereas the yield with respect to the converted pyrocatechol are practically the same as those of Example 3.

EXAMPLE 5

The procedure of Example 1 is followed, using 1,2-dichloroethane as solvent instead of the decalin. Gas chromatography analysis of the reaction mixture shows the following composition: o.methallyloxyphenol 54.7%, o.dimethyallyloxybenzene 1.1%, pyrocatechol 33.6%, o.methallylpyrocatechol 5.2%, p-methallylpyrocatechol 0.8%, o.isobutenylpyrocatechol 0.5%, various impurities 4.1%.

The conversion is 66.4%, the yield of o.methallyloxyphenol is 82% with respect to the converted pyrocatechol, and the yield of useful products (o.methallyloxyphenol, o.methallylpyrocatechol, o.isobutenylpyrocatechol) is 91% with respect to the converted pyrocatechol.

EXAMPLE 6

121 g (1.1 moles) of pyrocatechol, 880 ml of anisole, 51.6 g of TBAB (0.16 moles), 135.8 g of methallyl chloride (1.5 moles), 116.6 g of sodium carbonate (1.1 moles) and 1.8 g of sodium hydrosulphite are fed into a two liter four-neck reactor fitted with a condenser, stirrer, thermometer and nitrogen inlet. The reaction mixture is heated to 80° under stirring in a nitrogen atmosphere. After 3 hours of reaction, chromatography analysis shows a conversion of 57%.

After 6 hours of reaction, analysis shows the following composition of the reaction mixture: o.methallyloxybenzene 71.1%, o.dimethallyloxybenzene 1.8%, pyrocatechol 21%, o.methallylpyrocatechol 1.6%, o.isobutenylpyrocatechol 1.9%, various impurities 2.6%.

The conversion is 79%, the yield of o.methallyloxyphenol is 90% with respect to the converted pyrocatechol, and the yield of useful products (o.methallyloxyphenol, o.methallylpyrocatechol, o.isobutenylpyrocatechol) is 94.4% with respect to the converted pyrocatechol.

On repeating the test under the same conditions but with TBAB absent, it was found that only 3% of the pyrocatechol was converted after 3 hours, with an o.methallyloxyphenol yield of 70% with respect to the converted pyrocatechol.

The test was repeated under identical conditions, but with 400 ml of water present to form a double aqueous-organic phase.

After 6 hours of reaction, the conversion was 65.6% with an o.methallyloxyphenol yield of 61% with respect to the converted pyrocatechol.

Apart from the clearly lower conversions and yields, there are industrial difficulties in separating the two phases and recovering the products from the aqueous phase.

The test was repeated with all conditions kept as before, but using 44.8 g (1.1 moles) of NaOH in 20 ml of water instead of the sodium carbonate. A double aqueous-organic phase was also formed in this case, resulting in a phase transfer catalytic system. After 6 hours of reaction, the conversion was 74.6%, with an o.methallyloxyphenol yield of 35.6% with respect to the converted pyrocatechol.

In this case, the reaction was even less selective than in the preceding double phase test.

EXAMPLE 7

The procedure of Example 6 was followed, using isopropyl ether as solvent instead of the anisole. After heating for 6 hours at 69° C. in a nitrogen atmosphere, the reaction mixture demonstrated the following composition on gas chromatography analysis: o.methallyloxyphenol 35%, o.dimethallyloxybenzene 0.4%, pyrocatechol 63.6%, o.methallylpyrocatechol 0.3%, various impurities 0.6%.

The conversion is 36.4%, and the o.methallyloxybenzene yield is 96% with respect to the converted pyrocatechol.

EXAMPLE 8

The procedure of Example 6 was followed, using ethyl alcohol as solvent instead of anisole, and heating to 80° for 3 hours in a nitrogen atmosphere. Gas chromatography analysis shows the following reaction mixture composition when the reaction has terminated: o.methallyloxyphenol 76.8%, o.dimethallyloxybenzene 12.2%, pyrocatechol 3.1%, o.methallylpyrocatechol 3.2%, p.methallylpyrocatechol 0.3%, o.isobutenylpyrocatechol 3.5%, various impurities 1%.

The conversion is 96.9%, the yield of o.methallyloxyphenol is 79.3% with respect to the converted pyrocatechol, and the yield of useful products (o.methallyloxyphenol, o.methallylpyrocatechol, o.isobutenylpyrocatechol) is 86% with respect to the converted pyrocatechol.

EXAMPLE 9

121 g (1.1 moles) of pyrocatechol, 880 ml of o.dichlorobenzene, 51.6 g (0.16 moles) of TBAB, 135.8 g (1.5 moles) of methallylchloride, 116.6 g (1.1 moles) of sodium carbonate and 1.8 g of sodium hydrosulphite are fed into a two liter four-neck flask fitted with a condenser, stirrer, thermometer and nitrogen inlet. The mixture is heated to 80° for 6 hours in a nitrogen atmosphere. Gas chroatography analysis shows the following mixture composition at the end of the reaction: o.methallyloxyphenol 67.1%, o.dimethallyloxybenzene 1.2%, pyrocatechol 21%, o.methallylpyrocatechol 2.5%, o.isobutenylpyrocatechol 2.7%, various impurities 5.6%.

The conversion is 79%, the yield of o.methallyloxybenzene is 85% with respect to the converted pyrocatechol, and the yield of useful products (o.methallyloxyphenol, o.methallylpyrocatechol, o.isobutenylpyrocatechol) is 91.5%.

After cooling, the precipitated salts (essentially NaCl) are filtered off and washed with 20 ml of o.dichlorobenzene. The solution is washed with water to remove the TBAB and is then heated for 2 hours to 180°.

On gas chromatography analysis, the mixture obtained shows the presence of 73.6% of o.methallylpyrocatechol and 3.1% of 2,3-dihydro-2,2-dimethylbenzofuran-7-ol.

7.2 g of Amberlist 15 are then added to the cooled solution, and the mixture is heated under stirring for 6 hours to 80°. Gas chromatography analysis shows the presence of 68.3% of 2,3-dihydro-2,2-dimethylbenzofuran-7-ol in the total products present in the final solution. This product is recovered and purified by distillation under reduced pressure.

The first stage of the test was repeated in an identical manner, but without using the TBAB catalyst.

In this case, after 6 hours there was a pyrocatechol conversion of 20%, an o.methallyloxybenzene yield of 45% with respect to the converted pyrocatechol, and a total useful products yield of 48%.

EXAMPLE 10

The first stage of Example 9 was repeated using 1.1 moles of solid powdered NaOH instead of the sodium carbonate.

A pyrocatechol conversion of 73.7% was obtained, with an o.methallyloxybenzene yield of 67% and a total useful products yield of 86.5%.

EXAMPLE 11

121 g (1.1 moles) of pyrocatechol, 616 ml of decalin, 264 ml of ethanol, 135.8 g (1.5 moles) of methallyl chloride, 116.6 g of sodium carbonate, 1.8 g of sodium hydrosulphite and 51.6 g (0.16 moles) of TBAB are fed into a two liter four-neck reactor fitted with a condenser, stirrer, thermometer and nitrogen inlet. The mixture is heated to 80° under stirring in a nitrogen atmosphere. After 3 hours, gas chromatography analysis shows the following composition: o.methallyloxyphenol 68.8%, o.dimethallyloxybenzene 3%, pyrocatechol 23.7%, o.methallylpyrocatechol 1.8%, o.isobutenylpyrocatechol 1.7%, other impurities 1%. The conversion is 76.3%, the yield of o.methallyloxyphenol is 90% with respect to the converted pyrocatechol, and the yield of useful products (o.methallyloxyphenol, o.methallylpyrocatechol, o.isobutenylpyrocatechol) is 94% with respect to the converted pyrocatechol. The solution is then cooled, and the salts are filtered off and washed with 40 ml of ethanol.

The ethyl alcohol and unreacted methallyl chloride are removed under reduced pressure of 200–300 mg Hg.

Two phases separate on cooling. The upper phase (552 g), consisting of a decalin solution, shows on gas chromatography analysis 81.5% of o.methallyloxyphenol, 5% of o.methallyloxybenzene, 5% of pyrocatechol, 3.9% of o.methallylpyrocatechol, 0.4% of p.methallylpyrocatechol and 4.2% of various impurities.

This solution is heated to 180° for 2 hours, after which the composition of the dissolved products is as follows: o.methallylpyrocatechol 81.3%, pyrocatechol 4.1%, p.methallylpyrocatechol 12%, o.methallyloxyphenol 0.2%, o.dimethallyloxybenzene 0.6%, various impurities 1.8%.

16 g of Nafion 501 are added to the mixture obtained in this manner, and the temperature is adjusted to 80° for 9 hours. Gas chromatography analysis shows the following product composition in the final solution: 2,3-dihydro-2,2-dimethylbenzofuran-7-ol 79%, o.methallylpyrocatechol 5%, o.methallyloxyphenol 0.5%, o.dimethallyoxybenzene 0.5%, pyrocatechol 1.8%, various impurities 13%.

The 2,3-dihydro-2,2-dimethylbenzofuran-7-ol is separated from the final solution by distillation under reduced pressure.

A further 72.8 g of pyrocatechol, 616 ml of decalin, 264 ml of ethyl alcohol, 135.8 g of methallyl chloride, 116.6 g of sodium carbonate and 1.8 g of sodium hydrosulphite are added to the previously separated lower phase (140 g) which is constituted essentially by 48.2 g of pyrocatechol and the quaternary ammonium salt. The mixture is heated to 80° under stirring in a nitrogen atmosphere for 3 hours, to obtain practically the same results in o.methallyloxyphenol as obtained in the first cycle.

We claim:

1. A process for preparing 2,3-dihydro-2,2-dimethylbenzofuran-7-ol of formula

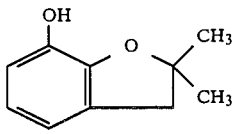
(I)

which process comprises the steps of: (a) selective monoetherification of pyrocatechol with a methallyl halide in the presence of an inorganic base in the solid state and a catalyst selected from the group consisting of quaternary ammonium salts, quaternary phosphonium salts and crown ethers; (b) thermal transposition of the o.methallyloxyphenol obtained in step (a) by heating the solution to a temperature of between 130° and 200° C.; and (c) cyclisation of the o.methallylpyrocatechol obtained in step (b) in the heterogeneous phase by stirring in the presence of an insoluble sulphonic acid resin catalyst at a temperature of between 10° and 150° C., said steps being carried out in a reaction medium consisting of inert organic solvent that remains a liquid at the elevated temperature of the process and in an inert gas atmosphere without separating intermediate products.

2. A process as claimed in claim 1, wherein the methallyl halide is methallyl chloride.

3. A process as claimed in claim 1, wherein the reaction between pyrocatechol and the methallyl halide is carried out at a temperature of between 40° and 120° C.

4. A process as claimed in claim 1, wherein the inorganic base in the solid state is sodium or potassium hydroxide or carbonate.

5. A process as claimed in claim 1, wherein the quaternary ammonium salt used as catalyst is of general formula

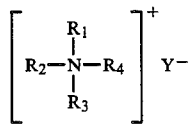

in which $R_1$, $R_2$, $R_3$, $R_4$ are equal or different $C_1$–$C_8$ hydrocarbon radicals, possibly substituted, and Y is a halide, sulphuric or sulphonic anion.

6. A process as claimed in claim 1, wherein the quaternary ammonium salt used as catalyst is of general formula

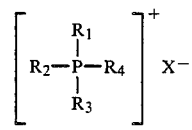

in which $R_1$, $R_2$, $R_3$, $R_4$ are $C_2$–$C_{10}$ hydrocarbon radicals, and X is a halide.

7. A process as claimed in claim 1, wherein the inert organic solvent is chosen from those solvent classes constituted by hydrocarbons, halogenated hydrocarbons, alcohols, ethers, ketones, nitriles and their mixtures, preferably having boiling points of between 130° and 200° C.

8. A process as claimed in claim 1, wherein the pyrocatechol and the methallyl halide are reacted in a molar ratio of between 0.5 and 1.5.

9. A process as claimed in claim 1, wherein the molar ratio of the pyrocatechol to the alkaline base is between 2 and 0.4.

10. A process as claimed in claim 1, wherein the catalyst in the form of the ammonium salt, phosphonium salt or crown ether is used in a quantity of between 0.01 and 0.8 moles per base equivalent.

11. A process as claimed in claim 6, wherein the halide ion is chloride or bromide.

12. A process as claimed in claim 1, wherein the catalyst of step (c) is used in a quantity of between 1 and 50% by weight of the o.methallylpyrocatechol.

13. A process as claimed in claim 1, wherein the reaction between pyrocatechol and the methallyl halide is carried out at a temperature of between 40° and 120° C., the inert organic solvent is selected from the group consisting of hydrocarbons, halogenated hydrocarbons, alcohol, ethers, ketones, nitriles and their mixtures, and the inert gas atmosphere is at atmospheric pressure.

14. A process as claimed in claim 13, wherein the organic solvent has a boiling point of between 130° and 200° C.

* * * * *